US010080827B2

(12) United States Patent
Buckberry (10) Patent No.: US 10,080,827 B2
(45) Date of Patent: Sep. 25, 2018

(54) BLOOD PUMP

(71) Applicant: Quanta Fluid Solutions Ltd., Alcester, Warwickshire (GB)

(72) Inventor: Clive Henry Buckberry, Warwick (GB)

(73) Assignee: Quanta Dialysis Technologies Limited, Warwickshire (GB)

( * ) Notice: Subject to any disclaimer, the term of this patent is extended or adjusted under 35 U.S.C. 154(b) by 499 days.

(21) Appl. No.: 14/779,794

(22) PCT Filed: Mar. 27, 2014

(86) PCT No.: PCT/GB2014/050977
§ 371 (c)(1),
(2) Date: Sep. 24, 2015

(87) PCT Pub. No.: WO2014/155119
PCT Pub. Date: Oct. 2, 2014

(65) Prior Publication Data
US 2016/0051739 A1      Feb. 25, 2016

(30) Foreign Application Priority Data

Mar. 28, 2013    (GB) .................................. 1305761.7

(51) Int. Cl.
*A61M 37/00*    (2006.01)
*A61M 1/10*     (2006.01)
(Continued)

(52) U.S. Cl.
CPC .......... *A61M 1/1048* (2014.02); *A61M 1/106* (2013.01); *A61M 1/1008* (2014.02);
(Continued)

(58) Field of Classification Search
CPC .............. A61M 1/1048; A61M 1/1008; A61M 1/1043; A61M 1/1065; A61M 1/3403;
(Continued)

(56) References Cited

U.S. PATENT DOCUMENTS 5,232,434 A      8/1993   Inagaki et al.
2008/0217245 A1  9/2008   Rambod et al.
(Continued)

FOREIGN PATENT DOCUMENTS

EP    1 674 119 A1    6/2006
EP    1 362 604 A1   11/2009
(Continued)

OTHER PUBLICATIONS

Sep. 29, 2015 International Preliminary Report on Patentability for PCT/GB2014/050977.

*Primary Examiner* — Philip R Wiest
(74) *Attorney, Agent, or Firm* — Hahn Loeser & Parks LLP (57) ABSTRACT

A blood pump comprising a cartridge, the cartridge comprising a first recess therein, said first recess having a surface, and a flexible diaphragm closing said first recess, the first recess and the flexible diaphragm defining a first pump chamber, said first pump chamber having an inlet and an outlet wherein the flexible diaphragm of the first pump chamber is movable between a first position, separated in use from the surface of the first recess, in which said first pump chamber has a maximum volume, and a second position, substantially adjacent to the surface of the first recess, in which said first pump chamber has a minimum volume a pump driver arranged to interface with the cartridge, said pump driver operable to move the flexible diaphragm of the first pump chamber in a first direction into said first recess to, in use, pump blood from the chamber and to move the flexible diaphragm of the first pump chamber in
(Continued)

a second direction away from the first recess to, in use, draw blood into said first pump chamber, wherein the pump driver controls the movement of the flexible diaphragm of the first pump chamber such that the flexible diaphragm of the first pump chamber moves toward said first position at a first speed and moves toward said second position at a second speed, said second speed being greater than said first speed.

20 Claims, 2 Drawing Sheets (51) Int. Cl.
  *A61M 1/36* (2006.01)
  *F04B 43/02* (2006.01)
  *F04B 49/20* (2006.01)
  *A61M 1/34* (2006.01)
(52) U.S. Cl.
  CPC ........ *A61M 1/1043* (2014.02); *A61M 1/1065* (2014.02); *A61M 1/1086* (2013.01); *A61M 1/34* (2013.01); *A61M 1/3403* (2014.02); *A61M 1/3607* (2014.02); *A61M 1/3612* (2014.02); *A61M 1/3639* (2013.01); *F04B 43/02* (2013.01); *F04B 49/20* (2013.01); *A61M 1/1006* (2014.02); *A61M 1/1037* (2013.01); *A61M 1/1063* (2014.02); *A61M 2205/12* (2013.01); *A61M 2205/3331* (2013.01); *A61M 2205/3334* (2013.01); *A61M 2205/3344* (2013.01)
(58) Field of Classification Search
  CPC .. A61M 1/3607; A61M 1/3612; A61M 1/106; A61M 1/1086; A61M 1/34; A61M 1/3639; A61M 1/1006; A61M 1/1063; A61M 1/1037; A61M 2205/3331; A61M 2205/3334; A61M 2205/3344; F04B 43/02; F04B 49/20
  USPC ................................................ 604/6.09–6.11
  See application file for complete search history.

(56) References Cited

U.S. PATENT DOCUMENTS

2009/0137940 A1\* 5/2009 Orr ....................... A61M 1/106
                                                    604/6.11
2011/0024353 A1\* 2/2011 Jonsson ................ A61M 1/106
                                                    210/637

FOREIGN PATENT DOCUMENTS

WO   WO 2009/127624 A2   10/2009
WO   WO 2013/121163 A1    8/2013

\* cited by examiner

BLOOD PUMP

The present application is a 35 USC § 371 submission of international application no, PCT/GB2014/050977, filed on 27 Mar. 2014 and published in the English language on 2 Oct. 2014 with publication no. WO 2014/155119 A1, which claims the benefit of the filing date of application no. GB 1305761.7, filed 28 Mar. 2013.

The present invention relates to extracorporeal blood pumps, in particular, but not exclusively, to low haemolysis extracorporeal blood pumps.

Blood pumps for the extracorporeal circulation of blood are used in a number of medical applications, for example in hemodialysis. Blood is pumped through hemodialysis machines using peristaltic type pumps. While peristaltic pumps are reliable and accepted within the medical industry, they can cause haemolysis in a patients blood, resulting in a lowered hematocrit level.

Haemolysis is the rupture of red blood cells and the releasing of their contents into surrounding blood plasma. Rupture of red blood cells alters the hematocrit level of the patients blood such that the proportion of red blood cells can fall below an optimal range of 40-45%.

When blood is returned to the patient after being treated in a hemodialysis machine, a reduced hematocrit level of the blood reduces the bloods ability to effectively transport oxygen in a patients body. As a result, many patients who have had extracorporeal blood treatment, such as hemodialysis, are treated with erythropoietin (EPO) to stimulate regeneration of new red blood cells to replace those damaged during treatment.

In some conditions requiring extracorporeal blood treatment, the patient needs to be treated with EPO to balance the hormonal requirements of the body. In patients suffering from such conditions, damage to blood cells results in an increase in the amount of EPO needed to be administered. Furthermore, when a patient has a naturally low hematocrit level due to a medical condition, for example end stage renal failure, damage to the red blood cells caused by extracorporeal treatment of the condition is particularly undesirable.

It is the purpose of the present invention to mitigate at least some of the above problems and to produce a blood pump that minimises damage to red blood cells.

A first aspect of the invention provides a blood pump comprising a cartridge, cartridge comprising a first recess therein, said first recess having a surface, and a flexible diaphragm closing said first recess, the first recess and the flexible diaphragm defining a first pump chamber, said first pump chamber having an inlet and an outlet wherein the flexible diaphragm of the first pump chamber is movable between a first position, separated in use from the surface of the first recess, in which said first pump chamber has a maximum volume, and a second position, substantially adjacent to the surface of the first recess, in which said first pump chamber has a minimum volume a pump driver arranged to interface with the cartridge, said pump driver operable to move the flexible diaphragm of the first pump chamber in a first direction into said first recess to, in use, pump blood from the chamber and to move the flexible diaphragm of the first pump chamber in a second direction away from the first recess to, in use, draw blood into said first pump chamber, wherein the pump driver controls the movement of the flexible diaphragm of the first pump chamber such that the flexible diaphragm of the first pump chamber moves toward said first position at a first speed and moves toward said second position at a second speed, said second speed being greater than said first speed.

An increase in speed of the flexible diaphragm of the first pump chamber between extremes of movement results in an increase in pulsatile flow of the patients blood which is advantageous in hemodialysis. Pulsatile flow occurs naturally in pumps having a variable output, such as membrane pumps. The variation in output of the pump causes pulses in fluid being pumped therethrough. By increasing the speed of the membrane between extremes of movement, the flow of blood through an output of the pump is increased accordingly during each pulse.

During hemodialysis treatment, a patients blood is effectively separated from a dialysate solution by a semi-permeable membrane. Waste materials from the patients blood pass through the membrane into the dialysate solution. Waste materials of small molecular size pass through the membrane by means of diffusion. Larger molecules of waste materials would not be able to breach a boundary layer of the semi-permeable membrane by diffusion alone. Increasing pulsatile flow of the patients blood, i.e. by increasing the range of output flow rates from the pump, increases disruption of the boundary layer and thus enables larger molecules of waste material to pass through the semi-permeable membrane into the dialysate solution. The patients blood, which is of an even greater molecular size than the waste maternal molecules, remains unable to pass through the semi-permeable membrane In one embodiment, the blood pump further comprises a platen, the platen having one or more recesses therein, each recess having a surface, the one or more recesses corresponding substantially in geometry to a recess in the cartridge and being separated therefrom by a flexible diaphragm associated therewith.

Advantageously, the surface(s) associated with the cartridge and the surface(s) associated with the platen provide a positive stop for the flexible diaphragm(s) thus defining the minimum and maximum volumes of the blood pump.

In one embodiment, the flexible diaphragm is pneumatically actuated between said first and second position.

In one embodiment, the flexible diaphragm, when in a first position contacts the surface of the first recess in the cartridge and, when in a second position contacts the surface of the corresponding recess in the platen.

A second aspect of the invention provides A blood pump comprising a cartridge, the cartridge comprising a first recess therein, said first recess having a surface, and a flexible diaphragm closing said first recess, the first recess and the flexible diaphragm defining a first pump chamber, said first pump chamber having an inlet and an outlet wherein the flexible diaphragm of the first pump chamber is movable between a first position, separated in use from the surface of the first recess, in which said first pump chamber has a maximum volume, and a second position, substantially adjacent to the surface of the first recess, in which said first pump chamber has a minimum volume; a pump driver arranged to interface with the cartridge, said pump driver operable to move the flexible diaphragm of the first pump chamber in a first direction into said first recess to, in use, pump blood from the chamber and to move the flexible diaphragm of the first pump chamber in a second direction away from the first recess to, in use, draw blood into said first pump chamber, wherein in a first operating mode, the flexible diaphragm moves toward said first position at a first speed and moves toward said second position at a second speed, said second speed being greater than said first speed and in a second operating mode, the flexible diaphragm moves toward said first position at substantially the same speed as it moves toward said second position.

In one embodiment, in the first operating mode, the blood pump draws blood from a patient and pumps it to a dialyser.

In one embodiment, in the second operating mode, the blood pump draws blood from the dialyser and pumps it back to the patient.

Advantageously, pumping a patients blood to the dialyser at a high velocity assists in disrupting the boundary layer of the semi-permeable membrane to permit a greater molecular size of waste material to pass through than is possible in conventional hemodialysis machines. Drawing blood from the patient at the same velocity could cause vascular damage hence control of the speed of the flexible diaphragm of the pump chamber is important to reduce the risk of such damage occurring.

A third aspect of the invention provides a blood pump comprising: a cartridge, the cartridge comprising a first recess therein, said first recess having a surface, and a flexible diaphragm closing said first recess, the first recess and the flexible diaphragm defining a first pump chamber, said first pump chamber having an inlet and an outlet wherein the flexible diaphragm of the first pump chamber is movable between a first position, separated in use from the surface of the first recess, in which said first pump chamber has a maximum volume, and a second position, substantially adjacent to the surface of the first recess, in which said first pump chamber has a minimum volume, the cartridge further comprising a second recess therein, said second recess having a surface, and a flexible diaphragm closing said second recess, said second recess and said flexible diaphragm defining a second pump chamber, said second pump chamber having an inlet and an outlet wherein the flexible diaphragm of the second pump chamber is movable between a first position, separated in use from the surface of the second recess, wherein in said first position said second pump chamber has a maximum volume, and a second position, substantially adjacent to said surface, wherein in said second position said second pump chamber has a minimum volume; a pump driver arranged to interface with the cartridge, said pump driver being operable to move the flexible diaphragms of the first and second pump chambers in a first direction into respective recesses to, in use, pump blood from the first and second pump chambers and to move the flexible diaphragm of the first and second pump chambers in a second direction away from the respective recesses of the first and second pump chambers to draw blood into said first and second pump chambers.

Provision of two pump chambers on the blood pump cartridge permits the blood pump to be used with single or twin needle configurations. A twin needle configuration is advantageous if greater flow of blood from the patient through the dialyser is required. Use of a twin needle configuration effectively allows for double the blood flow from the patient than use of a single needle configuration.

In one embodiment, the first and second pump chambers can be operated in phase with one another.

Operating the first and second pump chambers in phase with one another allows use of the twin needle configuration introduced above.

In another embodiment, the first and second pump chambers can be operated out of phase with one another.

Operating the first and second pump chambers out of phase with one another allows the first pump chamber, for example, to be used to draw blood from the patients artery and to pump blood to the dialyser and allows the second pump chamber, for example, to draw treated blood from the dialyser and return it to the patients vein.

In one embodiment, the flexible diaphragm of the first pump chamber moves toward said first position at a first speed and moves toward said second position at a second speed, said second speed being greater than said first speed.

In one embodiment, the flexible diaphragm of the second pump chamber moves toward said first position at a first speed and moves toward said second position at a second speed, said second speed being greater than said first speed.

In one embodiment, in a first operating mode, flexible diaphragm of the first pump chamber moves toward said first position at a first speed and moves toward said second position at a second speed, said second speed being greater than said first speed and in a second operating mode, the flexible diaphragm of the first pump chamber moves toward said first position at substantially the same speed as it moves toward said second position.

In one embodiment, in a first operating mode, the flexible diaphragm of the second pump chamber moves toward said first position at a first speed and moves toward said second position at a second speed, said second speed being greater than said first speed and in a second operating mode, the flexible diaphragm of the second pump chamber moves toward said first position at substantially the same speed as it moves toward said second position.

In one embodiment, the pump driver controls the movement of the flexible diaphragm such that the speed at which the diaphragm is moving reduces as it approaches said first and second positions.

In another embodiment, the pump driver controls the movement of the flexible diaphragm such that the speed at which the diaphragm is moving increases as it moves away from said first and second positions.

Preferably, on a first stroke of the pump, the speed of the flexible diaphragm increases gradually from zero to a predetermined maximum speed.

Preferably, on each subsequent stroke of the pump, any variation in speed as the flexible diaphragm approaches and moves away from said first and second positions is gradual.

In one embodiment, the variation in speed the flexible diaphragm as it approaches and moves away from said first and second positions is progressive.

In one embodiment, the variation in speed of the flexible diaphragm as it approaches and moves away from said first and second positions is non-linear.

In one embodiment, the blood pump further comprises an inlet valve to the first pump chamber and an inlet valve to the second pump chamber, each of said inlet valves being disposed in an inlet channel.

In one embodiment, the blood pump further comprises an outlet valve from the first pump chamber and an outlet valve from the second pump chamber, each outlet valve being disposed in an outlet channel.

The provision of inlet valves to and outlet valves from each pump chamber permits the first and second pump chambers to be used together, in isolation, in phase with each other or out of phase with each other. Such a configuration permits the blood pump to be used for either single needle or twin needle extracorporeal blood treatment.

In one embodiment, the pump driver controls the movement of the flexible diaphragms of the first and second pump chambers such that when the flexible diaphragm of the first pump chamber is in a first position, the flexible diaphragm of the second pump chamber is in a second position and when the flexible diaphragm of the first pump chamber is in a second position, the flexible diaphragm of the second pump chamber is in a first position. In other words, the pump chambers work alternately, or out of phase.

In one embodiment, the pump driver controls the movement of the flexible diaphragms of the first and second pump chambers such that when the flexible diaphragm of the first pump chamber is in a first position, the flexible diaphragm of the second pump chamber is in a first position and when the flexible diaphragm of the first pump chamber is in a second position, the flexible diaphragm of the second pump chamber is in a second position. In other words, the pump chambers work together or in phase.

In one embodiment, the blood pump further comprises a pressure transducer configured to measure the pressure of a patients blood passing through the blood pump, the pressure transducer being further configured to selectively control operation of the blood pump in response to the measured pressure of the patients blood deviating from a pre-determined range of values.

In one embodiment, the pressure transducer is located in a sensor cavity.

Preferably, the sensor cavity is located downstream of the first and/or second pump chamber.

In one embodiment, the cartridge further comprises one or more sensors cavities, the, or each, sensor cavity defining a recess in the cartridge, each sensor cavity recess having a surface, closable by a flexible diaphragm.

In one embodiment, each flexible diaphragm of the, or each, pump chamber and the, or each, sensor cavity is formed from a single common sheet of material applied to the cartridge.

In one embodiment, the sheet of material is vacuum attached to the cartridge in the region of the, or each, sensor cavity.

In one embodiment, the sheet of material is adhesively attached to the cartridge in the region of the, or each, pump chamber.

In one embodiment, the first pump chamber comprises a common inlet and outlet nd the second pump chamber comprises a common inlet and outlet.

In one embodiment, the first and second pump chambers each comprise two or more inlets and a corresponding number of outlets.

Embodiments of the invention will now be described, by way of example only, with reference to the following drawings in which.

Figure 1:
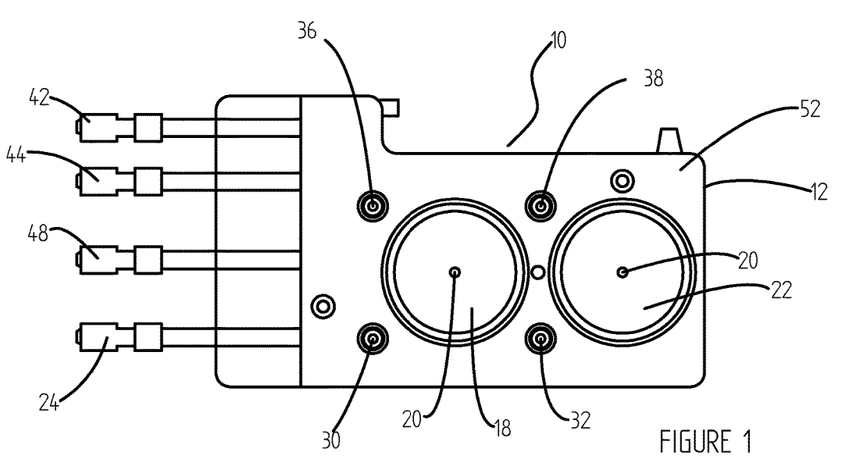
FIG. 1 is a schematic plan of a blood pump according to an embodiment of the invention viewed in a first direction.
Figure 2:
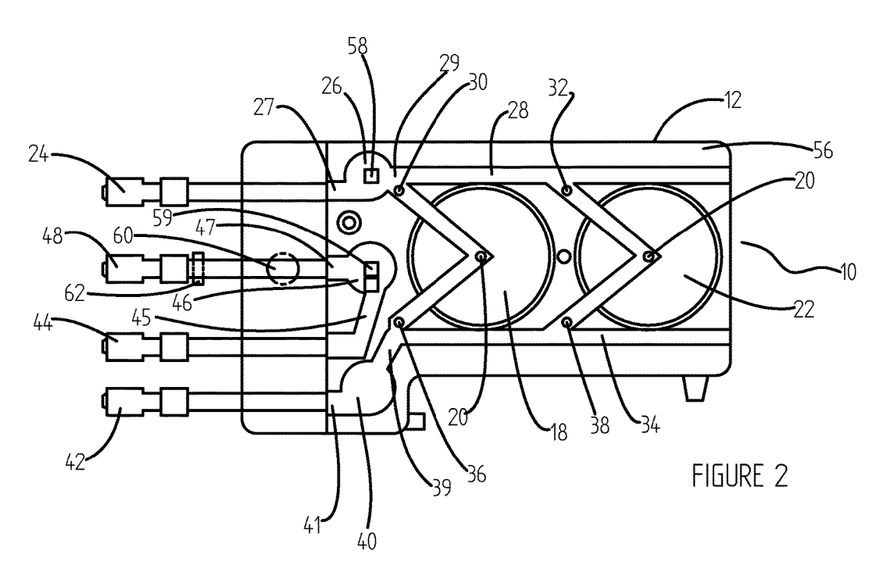
FIG. 2 is a schematic plan of a blood pump according to an embodiment of the invention viewed in a second direction.
Figure 3:
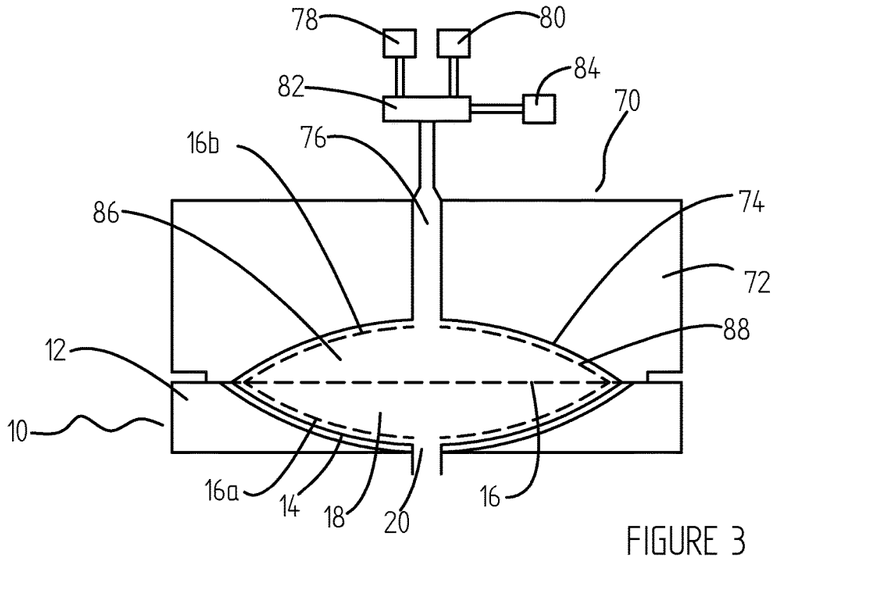
FIG. 3 is a schematic side view of a blood pump according to an embodiment of the invention.

Referring to FIGS. 1 to 3, an embodiment of the invention provides a blood pump 10 comprising a pump cartridge 12 manufactured from a plastic shell and having a concave recessed surface 14 covered by a flexible diaphragm 16. The recessed surface 14 and the flexible diaphragm 16 define a pump chamber 18 of conical, concave or frustoconical shape and having at the apex thereof a common inlet and outlet 20 for both allowing blood to flow into the pump chamber 18 and to be pumped from the pump chamber 18.

In the illustrated example, the cartridge 12 provides two pump chambers 18, 22 but it will be appreciated that the number of pump chambers is not intended to be limited. Blood is received via a needle from a patients artery through an arterial flow port 24 into a sensor cavity 26 defining an arterial pressure chamber. Blood enters the arterial pressure chamber 26 via an arterial pressure chamber inlet 27. The arterial pressure chamber 26 measures the pressure of blood from the patients artery and the output may be used to distinguish between a correctly placed needle and a dislodged needle. From the arterial pressure chamber 26 blood is received into an inlet channel 28, via an arterial pressure chamber outlet 29. The inlet channel 28 is provided with an inlet valve 30 to the first blood pump chamber 18 and an inlet valve 32 to the second blood pump chamber 22.

The first and second blood pump chambers 18, 22 are selectively operable to run in or out of phase with one another or in or out of phase with further pumps forming part of a hemodialysis machine. From the first and second blood pump chambers 18, 22, blood is pumped to an outlet channel 34, via an outlet valve 36 of the first blood pump chamber 18 and via an outlet valve 38 of the second blood pump chamber 22.

From the outlet channel 34 blood passes to a dialyser through a sensor cavity 40 defining a pre-dialyser pressure chamber. The pre-dialyser pressure chamber 40 has an inlet 39 and an outlet 41. Blood passes out of the cartridge 12 via a dialyser outlet port 42. The pre-dialyser pressure chamber 40 measures blood pressure prior to entering the dialyser to allow the flow rate of blood passing through the dialyser to be calculated.

After passing through the dialyser blood re-enters the cartridge 12 via a dialyser inlet port 44 into a sensor cavity 46 defining a venous pressure chamber. The venous pressure chamber 46 has an inlet 45 and an outlet 47. The venous pressure chamber 46 measures blood pressure blood prior to returning to the patients vein from the cartridge 12 via a venous outlet port 48. The venous pressure chamber 46 sends a signal to a modulated control valve 82 in response to variations in the venous return blood pressure caused by the patient moving around.

Each sensor cavity 26, 40, 46 comprises a concave recess covered by a flexible diaphragm to define the respective sensor cavity. The inlets and outlets from each sensor cavity are tangential to minimise stasis in the blood. Stasis occurs when flow of fluid is interrupted by an obstruction. Blood entering a sensor cavity through an inlet swirls within the sensor cavity until it exits through an outlet.

Although the illustrated embodiment is described having an arterial pressure chamber 26, venous pressure chamber 46 and pre-dialyser pressure chamber 40, the provided sensor cavities are not intended to be limited for such purposes. For example, the sensor cavities can be used for detecting pressure, bubbles, blood, hematocrit and urea clearance, for example by means of known apparatus and techniques. Additionally, although three sensor cavities are shown in the illustrated embodiment, it will be appreciated that more or less than three sensor cavities could be provided.

The arterial pressure chamber 46, of the illustrated embodiment, comprises a pressure transducer 58 for controlling a modulated valve 82 (see FIG. 3) provided on a hemodialysis machine, as described below. The pressure transducer 58 provides feedback to a controller 84 to prevent excessive vacuum being used to draw blood into the pump chamber(s) 18, 22, as described below.

The pump chambers, sensor cavities and valves all share a common datum face 52 covered by a single, common flexible sheet of material defining the respective pump chamber and sensor cavity diaphragms. In the illustrated embodiment, the inlet and outlet channels 28, 34 are provided on the opposing face 56 to the common datum face 52 of the cartridge and are closed by a second single, common flexible sheet of material (not shown).

In an alternative embodiment the inlet and outlet channels 28, 34 are disposed between and sealed by both flexible sheets of material.

The flexible sheet of material sealing the common datum surface 52 is held against the cartridge 12 by vacuum around each sensor cavity. The flexible sheet of material sealing the common datum surface 52 is attached by adhesive to the cartridge 12 at its periphery and around each pump chamber and valve to define the respective diaphragms. The flexible sheet of material (not shown) sealing the surface 56 opposing the common datum surface 52 is attached to the cartridge 12 by adhesive.

The cartridge 12 contains a thrombus trap 59 and a bubble trap 60, of known types, moulded therein in the form of flow through cells. The thrombus trap 59 could be located, for example, in a sensor cavity. The bubble trap 60 comprises a blood inlet (not shown), a blood outlet (not shown) and a vent (not shown) to the common datum face 52 side of the cartridge 12.

A venous clamp 62 is attached to the venous return line to the patient. Upon activation of a hemodialysis machine safety system, the venous clamp 62 is applied to prevent further flow of blood to the patient. In use, the safety system is adapted to also de-activate the blood pump chambers 18, 22 to prevent further blood being pumped from the patient.

With reference to FIG. 3, the cartridge 12 abuts a pump driver 70 (See FIG. 3) comprising a platen 72 having a recessed surface 74 therein and a fluid port 76. In use, the platen 70 is kinematically located against the cartridge 12 to sealingly engage with the cartridge 12 such that the recessed surface 74 and the flexible diaphragm 16 define a drive chamber 86. A sensor (not shown) detects whether the cartridge 12 is located correctly and generates an alarm signal if the cartridge 12 is incorrectly located. The cartridge 12 is held against the platen 70 by a door (not shown) and a sensor (not shown) detects whether the door is open or closed.

The fluid port 76 is connectable with a source of positive fluid pressure 78 and a negative source of fluid pressure 80 via a modulated valve 82, controlled by the controller 84 to allow fluid to flow into or out of the drive chamber 86.

The modulated valve 82 is a proportional valve having a variable sized orifice therein, the valve being controllable to change the size of the orifice, thereby controlling the flow of fluid therethrough.

The sources of positive and negative fluid pressure 78, 80 include a pressure pump and a vacuum pump respectively. When the modulated valve 82 is operated to allow fluid to flow into the drive chamber 86 from the source of positive fluid pressure 78, the flexible diaphragm 16a moves towards the recessed surface 14 and any blood that is in the pump chamber 18, 22 is pumped out of the common inlet and outlet 20. When the modulated valve 82 is operated to allow fluid to flow out of the drive chamber 86 to the source of negative fluid pressure 80, the flexible diaphragm 16b is moved away from the recessed surface 14 towards surface 74 and blood is drawn into the pump chamber 18, 22 from the common inlet and outlet 20.

In order to pump blood through the pump chambers 18, 22, the common inlet and outlet 20 of each pump 18, 22 has an inlet valve 30, 32 and an outlet valve 36, 38 associated therewith. In use, when the modulated valve 82 is operated to allow fluid into the drive chamber 86 from the source of positive fluid pressure 78, the inlet valve 30, 32 of the pump chamber 18, 22 is closed and the outlet valve 36, 38 of the pump chamber 18, 22 is open so that the blood within the pump chamber 18, 22 exits the common inlet and outlet 20 via the outlet valve 36, 38 of the pump chamber 18, 22.

When the modulated valve 82 is operated to allow fluid to flow out of the drive chamber 86 to the source of negative fluid pressure 80, the inlet valve 30, 32 of the pump chamber 18, 22 is opened and the outlet valve 36, 38 of the pump chamber 18, 22 is closed such that blood is drawn into the pump chamber 18, 22 through the common inlet and outlet 20 via the open inlet valve 30, 32 of the pump chamber 18, 22.

The inlet valves 30, 32 and outlet valves 36, 38 of the pump chambers 18, 22 are, in use, configured to operate to minimise pressure spikes in the patients blood.

When changing from filling to emptying the pump chamber 18, 22, the inlet valve 30, 32 of the pump chamber 18, 22 is closed and the outlet valve 36, 38 of the pump chamber 18, 22 is opened before flow of blood commences from the pump chamber. Opening the outlet valve 36, 38 of the pump chamber 18, 22 before flow of blood commences from the pump chamber 18, 22 ensures that there is no resistance against the flow of blood out of the common inlet and outlet 20. The outlet valve 36, 38 of the pump chamber 18, 22 is not opened instantaneously. Opening the outlet valve 36, 38 of the pump chamber 18, 22 at the same time as flow of blood commences from the pump chamber 18, 2.2 would create a positive pressure spike within the blood and cause rupturing of red blood cells.

When changing from emptying to filling the pump chamber 18, 22, the outlet valve 36, 38 of the pump chamber 18, 22 is closed and the inlet valve 30, 32 of the pump chamber 18, 2.2 is opened before flow of blood commences to the pump chamber 18, 22. Opening the inlet valve 30, 32 of the pump chamber 18, 22 before flow of blood commences to the pump chamber 18, 22 ensures that there is no resistance against the flow of blood into the common inlet and outlet 20 of the pump chamber 18, 22. The inlet valve 30, 32 of the pump chamber 18, 22 is not opened instantaneously. Opening the inlet valve 30, 32 of the pump chamber 18, 22 at the same time as flow of blood commences into the pump chamber 18, 22 would create a negative pressure spike within the blood and cause rupturing of red blood cells.

The inlet valves 30, 32 and the outlet valves 36, 38 of the pump chambers 18, 22 may be operated such that when the flexible diaphragm 16 of a pump chamber 18, 22 is at one extremity of its travel, either adjacent the concave recess 14 or adjacent the recessed surface 72, the valve of the pump chamber 18, 22, that is opening opens before the valve of the pump chamber 18, 22 that is closing closes, i.e. both valves of the pump chamber are momentarily open.

For example, when positive pressure is applied to the flexible diaphragm 16 it travels in the direction towards the concave recess 14, displacing blood through the common inlet and outlet 20 via the open outlet valve 36, 38 of the pump chamber 18, 22.

Once the flexible diaphragm 16a has reached the concave recess 14, the inlet valve 30, 32 of the pump chamber 18, 22 is first opened, the outlet valve 36, 38 of the pump chamber 18, 22 is then closed and then the modulated valve 82 is operated to allow fluid to flow out of the drive chamber 86 such that the flexible diaphragm 16 starts to move in the direction away from the concave recess 14 and towards the recessed surface 72.

In a similar manner, when the diaphragm 16b reaches the extremity of its travel adjacent the recessed surface 72, the outlet valve 36, 38 of the pump chamber 18, 22 is first opened, the inlet valve 30, 32 of the pump chamber 18, 22 is then closed, and the modulated valve 82 is then operated to allow fluid to flow into the drive chamber 86 such that the flexible diaphragm 16b starts to move in the direction away from the recessed surface 72 and towards the concave recess 14.

The controller 84 is operable to variably open the modulated valve 82 such that on the first stroke of the flexible diaphragm into, or out of, the pump chamber 18, 22, fluid flow is gradually increased from zero before being increased to a pre-determined constant fluid flow rate. The flow rate is increased to a maximum as the flexible diaphragm 16 passes the mid-point of each cycle to maximise the efficiency of the pumping duty cycle.

The blood pump 10 has two operating modes, firstly to draw blood from a patient and pump the blood to a dialyser. Secondly, to draw treated blood from the dialyser and return the blood to the patient. Blood is drawn from the patient at a flow rate corresponding to the speed of movement of the flexible diaphragm 16 of the pump chamber 18, 22 towards a first position 16b. The flexible diaphragm 16 of the pump chamber 18, 22 moves towards a first position 16b at a first speed. This is the same in both operating modes.

In the first operating mode, blood is pumped to the dialyser at a flow rate corresponding to the speed of movement of the flexible diaphragm 16 of the pump chamber 18, 22 towards a second position 16a. The flexible diaphragm 16 of the pump chamber 18, moves towards the second position 16a at a second speed. The second speed is greater than the first speed.

In the second operating mode, the flexible diaphragm of the pump chamber moves towards both the first and second positions at substantially the same speed.

The controller 84 is also operable to variably close the modulated valve 82 such that as the flexible diaphragm 16a, 16b reaches the end of its movement, fluid flow is gradually reduced and does not stop abruptly. A gradual reduction in the speed of the flexible diaphragm avoids fluid hammer within the blood which causes rupture of red blood cells. Furthermore, as the flexible diaphragm 16a approaches the recessed surface 14, the blood flows through the common inlet and outlet 20 and therefore, if the flexible diaphragm 16 were to be operated at a single speed, would accelerate through the common inlet and outlet thus increasing fluid shear on red blood cells. Reducing the speed of the flexible diaphragm 16a, 16b at the end of each pump stroke reduces the severity of any shear forces acting on a patients blood cells and therefore reduces the occurrence of lowered hematocrit levels in the patients blood, due to hemolysis.

The controller 84 closes the modulated valve 82 upon detection of an arterial blood pressure outside of a pre-determined range. The controller variably opens and closes the modulated valve 82 in response to variations in the venous return blood pressure caused by the patient moving around.

Although the blood pump(s) is/are described with reference to a pump chamber 18, 22 having a single common inlet and outlet 20, each pump chamber 18, 22 could also be provided with two inlet ports and two outlet ports while having the same effect in minimising stasis within the patients blood. Each pump chamber 18, 22 could also be provided with more than two inlet ports and a corresponding number of outlet ports.

Figure 4:
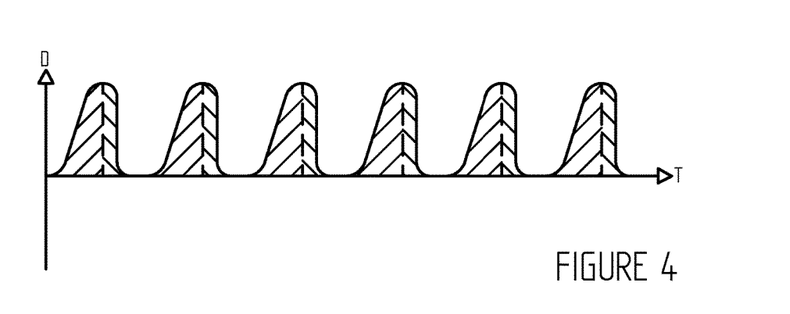
FIG. 4 is the characteristic of displacement (D) against time (t) for an operating mode of the flexible diaphragm of an embodiment of the invention.

FIG. 4 shows a profile of movement of the flexible diaphragm, in a first operating mode, where t=time and where D=displacement of blood within the pump chamber. The profile shows that in the first operating mode, blood is drawn into the pump chamber at a first flow rate and expelled from the pump chamber at a second flow rate. The second flow rate is greater than the first flow rate.

In another embodiment, the blood pump is a disposable blood pump comprising a disposable pump cartridge.

The embodiments of the invention, described with reference to the figures, are examples only and do not exclude variations therefrom from the scope of the invention as defined by the claims.

The invention claimed is:

1. A blood pump comprising:
   a cartridge, the cartridge comprising a first recess therein, said first recess having a surface, and a first flexible diaphragm closing said first recess, the first recess and the first flexible diaphragm defining a first pump chamber, said first pump chamber having a common inlet and outlet, wherein the first flexible diaphragm of the first pump chamber is movable between a first position, separated in use from the surface of the first recess, in which said first pump chamber has a maximum volume, and a second position, substantially adjacent to the surface of the first recess, in which said first pump chamber has a minimum volume;
   a pump driver arranged to interface with the cartridge, said pump driver operable to move the first flexible diaphragm of the first pump chamber in a first direction into said first recess to, in use, pump blood from the chamber, and to move the first flexible diaphragm of the first pump chamber in a second direction away from the first recess to, in use, draw blood into said first pump chamber;
   wherein the pump driver controls the movement of the first flexible diaphragm of the first pump chamber such that the first flexible diaphragm of the first pump chamber moves toward said first position at a first speed and moves toward said second position at a second speed, said second speed being greater than said first speed.

2. The blood pump according to claim 1, wherein the cartridge further comprises a second recess therein, said second recess having a surface, and a second flexible diaphragm closing said second recess, said second recess and said second flexible diaphragm defining a second pump chamber, said second pump chamber having an inlet and an outlet, wherein the second flexible diaphragm of the second pump chamber is movable between a first position, separated in use from the surface of the second recess, in which said second pump chamber has a maximum volume, and a second position, substantially adjacent to said surface of the second recess, in which said second pump chamber has a minimum volume.

3. The blood pump according to claim 1, wherein the pump driver controls the movement of the first flexible diaphragm of the first pump chamber such that the speed at which the first flexible diaphragm of the first pump chamber is moving reduces as it approaches said first and second positions.

4. The blood pump of claim 1, wherein the common inlet and outlet is arranged in a center of the first recess.

5. A blood pump comprising:
   a cartridge, the cartridge comprising a first recess therein, said first recess having a surface, and a first flexible diaphragm closing said first recess, the first recess and the first flexible diaphragm defining a first pump chamber, said first pump chamber having an inlet and an outlet, wherein the first flexible diaphragm of the first pump chamber is movable between a first position, separated in use from the surface of the first recess, in which said first pump chamber has a maximum volume, and a second position, substantially adjacent to the surface of the first recess, in which said first pump chamber has a minimum volume;
a pump driver arranged to interface with the cartridge, said pump driver operable to move the first flexible diaphragm of the first pump chamber in a first direction into said first recess to, in use, pump blood from the chamber, and to move the first flexible diaphragm of the first pump chamber in a second direction away from the first recess to, in use, draw blood into said first pump chamber;
wherein, in a first operating mode, the first flexible diaphragm moves toward said first position at a first speed and moves toward said second position at a second speed, said second speed being greater than said first speed and, in a second operating mode, the first flexible diaphragm moves toward said first position at substantially the same speed as it moves toward said second position.

6. The blood pump according to claim 5, wherein, in the first operating mode, the blood pump draws blood from a patient and pumps it to a dialyser.

7. The blood pump according to claim 6, wherein, in the second operating mode, the blood pump draws the blood from the dialyser and pumps it back to the patient.

8. The blood pump of claim 5,
wherein the cartridge further comprises a second recess therein, the second recess having a surface, and a second flexible diaphragm closing the second recess, the second recess and the second flexible diaphragm defining a second pump chamber, the second pump chamber having an inlet and an outlet, wherein the second flexible diaphragm of the second pump chamber is movable between a first position, separated in use from the surface of the second recess, in which the second pump chamber has a maximum volume, and a second position, substantially adjacent to the surface of the second recess, in which the second pump chamber has a minimum volume; and
wherein the pump driver is operable to move the second flexible diaphragm of the second pump chamber in a first direction into the second recess to, in use, pump blood from the second pump chamber, and to move the second flexible diaphragm of the second pump chamber in a second direction away from the second recess to, in use, draw blood into the second first pump chamber.

9. The blood pump of claim 8, wherein, in a first operating mode, the second flexible diaphragm moves toward its first position at a first speed and moves toward its second position at a second speed, said second speed being greater than said first speed and, in a second operating mode, the second flexible diaphragm moves toward its first position at substantially a same speed as it moves toward its second position.

10. A blood pump comprising:
a cartridge, the cartridge comprising a first recess therein, said first recess having a surface, and a first flexible diaphragm closing said first recess, the first recess and the first flexible diaphragm defining a first pump chamber having a common inlet and outlet, wherein the first flexible diaphragm of the first pump chamber is movable between a first position, separated in use from the surface of the first recess, in which said first pump chamber has a maximum volume, and a second position, substantially adjacent to the surface of the first recess, in which said first pump chamber has a minimum volume; the cartridge further comprising a second recess therein, said second recess having a surface, and a second flexible diaphragm closing said second recess, said second recess and said second flexible diaphragm defining a second pump chamber having a common inlet and outlet, wherein the second flexible diaphragm of the second pump chamber is movable between a first position, separated in use from the surface of the second recess, in which said second pump chamber has a maximum volume, and a second position, substantially adjacent to said surface of the second recess, in which said second pump chamber has a minimum volume;
a pump driver arranged to interface with the cartridge, said pump driver operable to move the flexible diaphragms of the first and second pump chambers in a first direction into respective recesses to, in use, pump blood from the first and second pump chambers, and to move the flexible diaphragms of the first and second pump chambers in a second direction away from the respective recesses of the first and second pump chambers to draw blood into said first and second pump chambers.

11. The blood pump according to claim 10, wherein the pump driver controls the movement of the first and second flexible diaphragms of the first pump chamber and the second pump chamber such that the speed at which the first flexible diaphragm is moving is reduced as it approaches its first and second positions, and the speed at which the second flexible diaphragm is moving is reduced as it approaches its first and second positions.

12. The blood pump according to claim 10, wherein the pump driver controls the movement of the flexible diaphragms of the first and second pump chambers such that when the first flexible diaphragm is in its first position, the second flexible diaphragm is in its second position, and when the first flexible diaphragm is in its second position, the second flexible diaphragm is in its first position.

13. The blood pump according to claim 10, wherein the pump driver controls the movement of the first and second flexible diaphragms such that when the first flexible diaphragm is in its first position, the second flexible diaphragm is in its first position, and when the first flexible diaphragm is in its second position, the second flexible diaphragm is in its second position.

14. The blood pump according to claim 10, further comprising:
a pressure transducer configured to measure pressure of a patient's blood passing through the blood pump, the pressure transducer being further configured to selectively control operation of the blood pump in response to the measured pressure of the patient's blood deviating from a pre-determined range of values.

15. The blood pump according to claim 14, wherein the pressure transducer is downstream of the first pump chamber.

16. The blood pump according to claim 10, wherein the pump driver controls the movement of the first and second flexible diaphragms such that the speed at which the first flexible diaphragm is moving between its first and second positions is maximal at a position between its first and second positions, and the speed at which the second flexible diaphragm is moving between its said first and second positions is maximal at a position between its first and second positions.

17. The blood pump according to claim 10,
wherein the first flexible diaphragm moves toward its first position at a first speed and moves toward its second position at a second speed, said second speed being greater than said first speed; and
wherein the second flexible diaphragm moves toward its first position at a first speed and moves toward its second position at a second speed, said second speed of the second flexible diaphragm being greater than said first speed of the second flexible diaphragm.

18. The blood pump according to claim 10, wherein, in a first operating mode, the first flexible diaphragm moves toward its first position at a first speed and moves toward its second position at a second speed, said second speed being greater than said first speed and, in a second operating mode, the first flexible diaphragm moves toward its first position at substantially the same speed as it moves toward its second position.

19. The blood pump according to claim 18, wherein, in the first operating mode, the second flexible diaphragm moves toward its first position at a first speed and moves toward its second position at a second speed, said second speed being greater than said first speed and, in a second operating mode, the second flexible diaphragm moves toward its said first position at substantially the same speed as it moves toward its second position.

20. The blood pump of claim 10, wherein the common inlet and outlet of the first pump chamber is arranged in a center of the first recess, and the common inlet and outlet of the second pump chamber is arranged in a center of the second recess.

* * * * *

UNITED STATES PATENT AND TRADEMARK OFFICE
CERTIFICATE OF CORRECTION

PATENT NO. : 10,080,827 B2
APPLICATION NO. : 14/779794
DATED : September 25, 2018
INVENTOR(S) : Clive Henry Buckberry It is certified that error appears in the above-identified patent and that said Letters Patent is hereby corrected as shown below:

In the Specification

In Column 9, Line 27, delete "chamber 18, moves" and substitute therefor --chamber 18, 22 moves--.

Signed and Sealed this
Twenty-fifth Day of June, 2019

Andrei Iancu
*Director of the United States Patent and Trademark Office*